United States Patent
Takeda et al.

(10) Patent No.: US 9,619,722 B2
(45) Date of Patent: Apr. 11, 2017

(54) GAZE DIRECTION DETECTION DEVICE, AND GAZE DIRECTION DETECTION METHOD

(71) Applicant: Panasonic Intellectual Property Management Co., Ltd., Osaka (JP)

(72) Inventors: Hidetoshi Takeda, Osaka (JP); Masayuki Kimura, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 32 days.

(21) Appl. No.: 14/886,188

(22) Filed: Oct. 19, 2015

(65) Prior Publication Data

US 2016/0042240 A1 Feb. 11, 2016

Related U.S. Application Data

(63) Continuation of application No. PCT/JP2014/005435, filed on Oct. 28, 2014.

(30) Foreign Application Priority Data

Nov. 1, 2013 (JP) ................................. 2013-227926

(51) Int. Cl.
*G06K 9/00* (2006.01)
*A61B 5/18* (2006.01)
(Continued)

(52) U.S. Cl.
CPC ............ *G06K 9/00845* (2013.01); *A61B 5/18* (2013.01); *G06K 9/0061* (2013.01);
(Continued)

(58) Field of Classification Search
USPC ........................................................ 382/104
See application file for complete search history.

(56) References Cited

U.S. PATENT DOCUMENTS

| 5,576,796 A | 11/1996 | Akashi |
| 5,745,174 A * | 4/1998 | Nakano ................. G03B 13/02 348/333.03 |

(Continued)

FOREIGN PATENT DOCUMENTS

| JP | 7-151958 | 6/1995 |
| JP | 9-238905 | 9/1997 |
| JP | 2005-261728 | 9/2005 |
| JP | 2010-029262 | 2/2010 |
| JP | 2010-030361 | 2/2010 |

OTHER PUBLICATIONS

International Search Report of PCT application No. PCT/JP2014/005435 dated Dec. 22, 2014.

*Primary Examiner* — Ishrat I Sherali
(74) *Attorney, Agent, or Firm* — Wenderoth, Lind & Ponack, L.L.P.

(57) ABSTRACT

A gaze direction detection device according to the present technology includes a detector for detecting a gaze of a driver over a predetermined period of time, a determiner for outputting second gaze information indicating that the driver is gazing, from first gaze information detected by the detector, a generator for generating a gaze distribution from the second gaze information output by the determiner, and a corrector for correcting the first gaze information detected by the detector, where the corrector calculates a center of a reference distribution that is set in advance and a center of the gaze distribution generated by the generator, and causes the center of the reference distribution and the center of the gaze distribution to overlap each other, and then calculates a correction parameter based on a difference between the reference distribution and the gaze distribution, and corrects the first gaze information with the correction parameter.

5 Claims, 10 Drawing Sheets

(51) Int. Cl.
*G06T 7/73* (2017.01)
*A61B 3/113* (2006.01)
*G08G 1/16* (2006.01)

(52) U.S. Cl.
CPC ............ *G06K 9/00597* (2013.01); *G06T 7/73* (2017.01); *A61B 3/113* (2013.01); *G06T 2207/10021* (2013.01); *G06T 2207/10048* (2013.01); *G06T 2207/30201* (2013.01); *G06T 2207/30268* (2013.01); *G08G 1/16* (2013.01)

(56) References Cited

U.S. PATENT DOCUMENTS

| | | | |
|---|---|---|---|
| 7,460,940 B2 | 12/2008 | Larsson et al. | |
| 7,783,077 B2* | 8/2010 | Miklos | G06F 3/013 351/209 |
| 7,815,313 B2* | 10/2010 | Ito | G08G 1/167 340/425.5 |
| 8,538,044 B2* | 9/2013 | Tsukizawa | A61B 3/113 381/117 |
| 8,824,779 B1* | 9/2014 | Smyth | G06K 9/0061 382/100 |
| 8,937,536 B2* | 1/2015 | Hatakeyama | B60K 35/00 340/435 |
| 9,096,233 B2* | 8/2015 | Mizutani | G08G 1/16 |
| 9,245,171 B2* | 1/2016 | Aoki | G06K 9/00221 |
| 2012/0200490 A1 | 8/2012 | Inada | |

* cited by examiner

GAZE DIRECTION DETECTION DEVICE, AND GAZE DIRECTION DETECTION METHOD

BACKGROUND

1. Field

The present technology relates to a gaze direction detection device and a gaze direction detection method for detecting a gaze direction of a driver in a driving support device for supporting driving operation of a driver driving a vehicle.

2. Description of the Related Art

As a technology for detecting a gaze direction in a non-contact manner, there is known a corneal reflection method. The corneal reflection method detects the gaze direction by measuring, based on an image of an eye shot by a camera, a positional relationship between the pupil and a reflected image (Purkinje image) that is formed by radiating near-infrared light of an LED or the like on the cornea. With the corneal reflection method, before performing measurement, so-called calibration of obtaining a correction factor for each person to be measured and of reducing an error due to individual differences is performed.

Unexamined Japanese Patent Publication No. 7-151958 discloses a technology of updating, during operation of an appliance, a parameter that is used for calculation of gaze information by providing an update means for updating a parameter in a storage means based on the gaze information during operation of the appliance.

SUMMARY

A gaze direction detection device according to the present technology includes a detector for detecting a gaze of a driver over a predetermined period of time, a determiner for outputting second gaze information indicating that the driver is gazing, from first gaze information detected by the detector, a generator for generating a gaze distribution from the second gaze information output by the determiner, and a corrector for correcting the first gaze information detected by the detector, where the corrector calculates a center of a reference distribution that is set in advance and a center of the gaze distribution generated by the generator, and causes the center of the reference distribution and the center of the gaze distribution to overlap each other, and then calculates a correction parameter based on a difference between the reference distribution and the gaze distribution, and corrects the first gaze information with the correction parameter.

DETAILED DESCRIPTION

Hereinafter, description will be given with reference to the drawings as appropriate taking, as an example, a case where a gaze direction detection device according to an exemplary embodiment of the present technology is applied to a driving support device for supporting driving operation of a driver.

However, unnecessarily detailed description may be omitted. For example, detailed description of already well-known matters and repetition of substantially the same configuration may be omitted. All of such omissions are intended to facilitate understanding by those skilled in the art by preventing the following description from becoming unnecessarily redundant.

Moreover, the applicant provides the appended drawings and the following description for those skilled in the art to fully understand the present technology, and does not intend to limit the subject described in the claims by the appended drawings and the following description.

Figure 1:
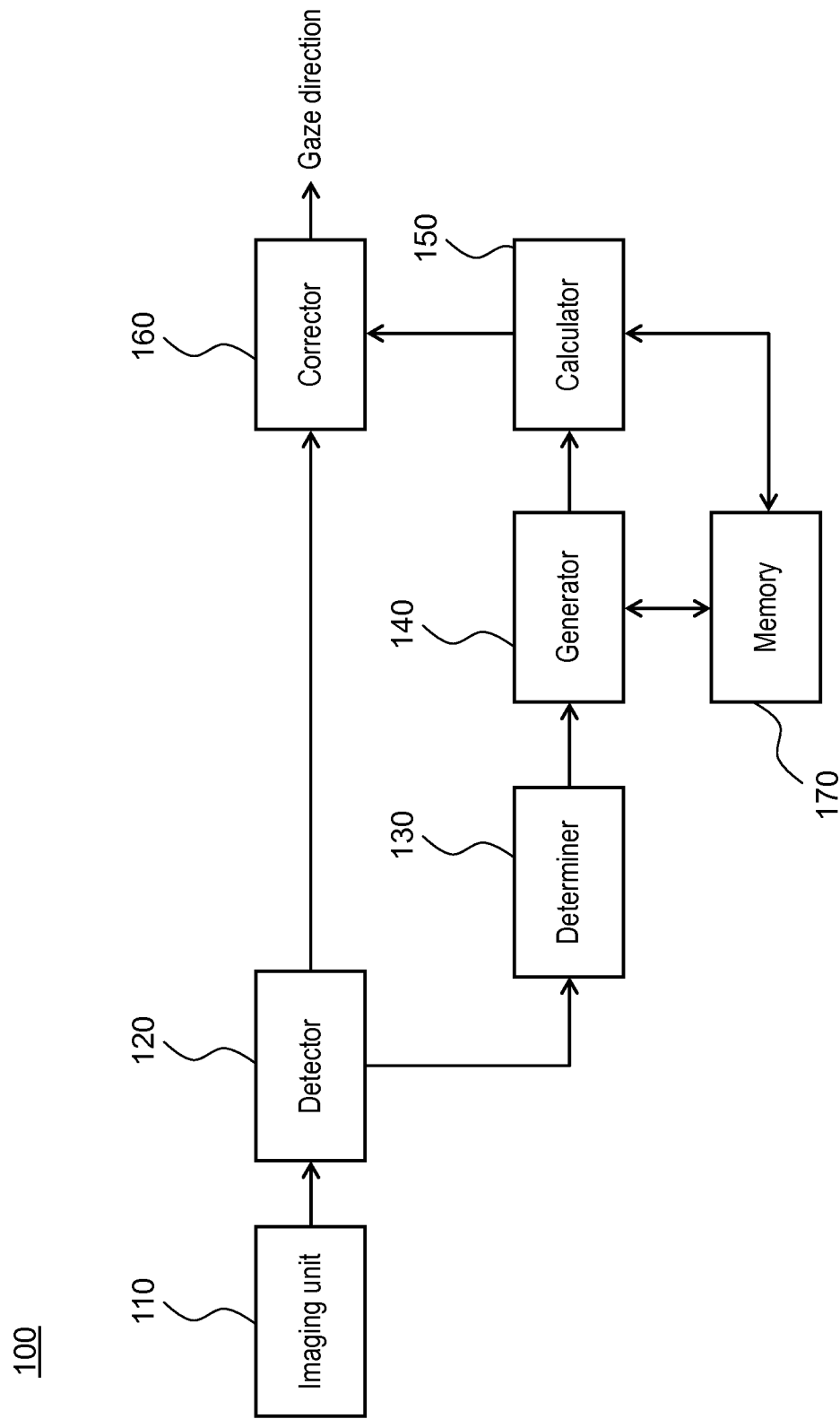
FIG. 1 is a block diagram showing a configuration example of a gaze direction detection device according to an exemplary embodiment of the present technology.
Figure 2:
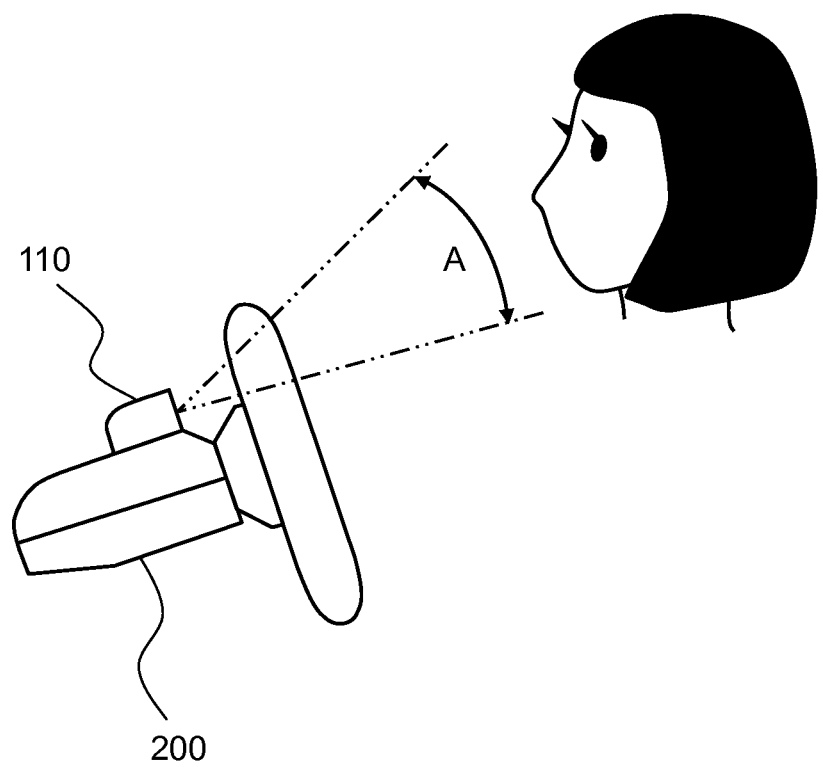
FIG. 2 is an explanatory diagram showing an installation example of an imaging unit of a gaze direction detection device according to an exemplary embodiment of the present technology.
Figure 3:
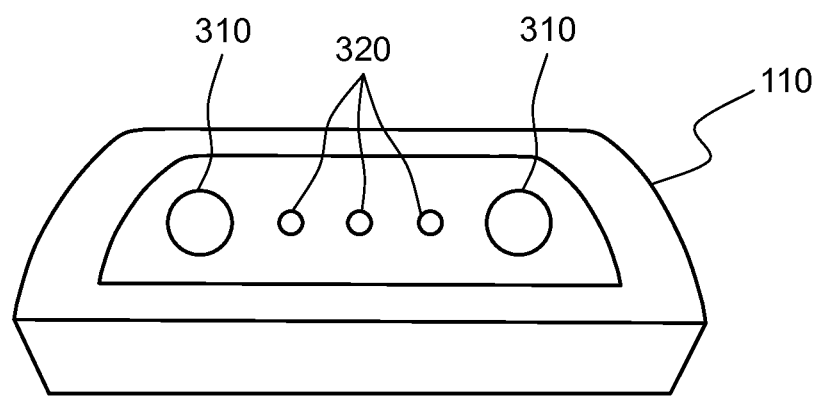
FIG. 3 is an explanatory diagram showing a configuration example of an imaging unit of a gaze direction detection device according to an exemplary embodiment of the present technology.

FIG. 1 is a block diagram showing configuration example of a gaze direction detection device according to an exemplary embodiment of the present technology. FIG. 2 is an explanatory diagram showing an installation example of an imaging unit of a gaze direction detection device according to an exemplary embodiment of the present technology. FIG. 3 is an explanatory diagram showing a configuration example of the imaging unit shown in FIG. 2.

As shown in FIG. 1, gaze direction detection device 100 includes imaging unit 110, detector 120, determiner 130, generator 140, calculator 150, corrector 160, and memory 170.

As shown in FIG. 2, imaging unit 110 is installed on top of steering column 200 of a vehicle, and captures the face of a driver. Imaging unit 110 is an infrared camera with angle of view A, for example, and captures the face of the driver by receiving reflected light of radiated near-infrared light.

Imaging unit 110 outputs, to detector 120, an image signal of a captured image as a detection signal. Additionally, imaging unit 110 may be installed at any position, such as at the dashboard or inside the meter panel, as long as the face of the driver may be shot from the direction as close as possible to a front direction of the face of the driver.

Furthermore, as shown in FIG. 3, imaging unit 110 is a stereo camera including near-infrared light sources 320, such as LEDs, to be used for lighting between two cameras 310 arranged with a gap of a predetermined distance, such as 3 cm. For example, imaging unit 110 shoots 30 images per second, and outputs image signals to detector 120. Additionally, the configuration of imaging unit 110 is not limited to the configuration in FIG. 3, and light sources 320 of LEDs may be installed outside each of cameras 310.

Next, detector 120 detects gaze information (first gaze information) such as a gaze direction (angle) or a viewpoint position by using the detection signals output by imaging unit 110. The gaze information is output to determiner 130 and corrector 160. For example, detector 120 detects the gaze direction by using a corneal reflection method. Also, detector 120 obtains a three-dimensional position of a viewpoint by obtaining a disparity between the viewpoints from two images captured by imaging unit 110, which is a stereo camera.

Determiner 130 determines, based on the first gaze information output from detector 120, whether the driver is continuously facing (gazing) approximately the same direction during a period of a predetermined number of frames or a predetermined period of time of 0.3 seconds for example. Determiner 130 selects, among pieces of first gaze information output from detector 120, only second gaze information where gazed by the driver is determined, and outputs the same to generator 140. In other words, determiner 130 performs operation of not outputting gaze information where movement of the gaze is assumed. Additionally, the second gaze information to be output may be all the pieces of gaze information in a predetermined period of time, or at least one piece of gaze information may be selected from the predetermined period of time and be output.

Generator 140 accumulates the second gaze information output from determiner 130 in memory 170 over a predetermined period of time, and generates a gaze distribution obtained from the pieces of second gaze information. The predetermined period of time may be five minutes, for example, but this is not restrictive, and the period of time may be any period of time until a predetermined number of pieces of gaze information are accumulated, such as 3000 seconds, so as to allow accumulation of a sufficient number of pieces of gaze information for the gaze distribution to be generated.

Figure 4:
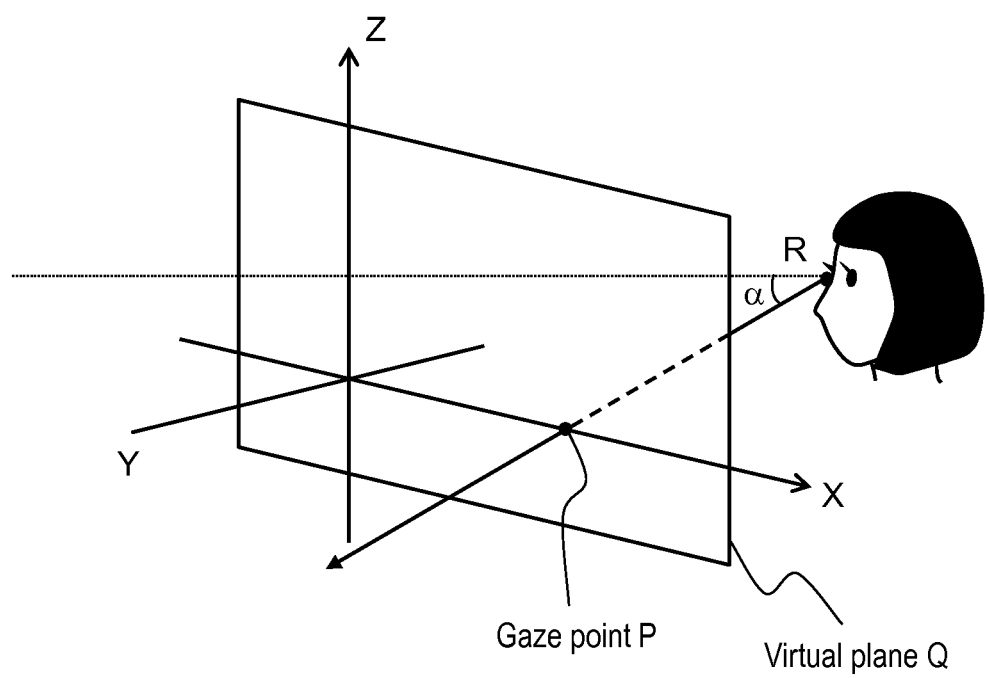
FIG. 4 is an explanatory diagram for describing an example of a gaze position detection method of a gaze direction detection device according to an exemplary embodiment of the present technology.

FIG. 4 is an explanatory diagram for describing an example of a gaze position detection method, and is a diagram for describing accumulation operation of generator 140.

As shown in FIG. 4, virtual plane Q is provided at a position about three meters in front of a seat. Gaze point P on virtual plane Q is obtained by using the gaze direction (angle α) included in the gaze information output by determiner 130 and viewpoint position R, and is accumulated in memory 170. Gaze point P is a point that intersects with virtual plane Q when drawing a straight line from viewpoint position R in the gaze direction. By obtaining gaze point P in this manner, even if the viewpoint position or the position of the face moves, gaze point P on the same virtual plane Q may be accumulated. Additionally, virtual plane Q is provided in FIG. 4, but a virtual spherical surface may also be provided instead. Also, virtual plane Q is provided about three meters in front of the driver, but this is not restrictive.

Generator 140 generates a gaze distribution from a plurality of gaze points accumulated in memory 170, and outputs the same to calculator 150. Additionally, generator 140 may alternatively cause the gaze distribution to be stored in memory 170 instead of outputting the same to calculator 150, and may output, to calculator 150, information indicating a storage area of the gaze distribution in memory 170.

Figure 5:
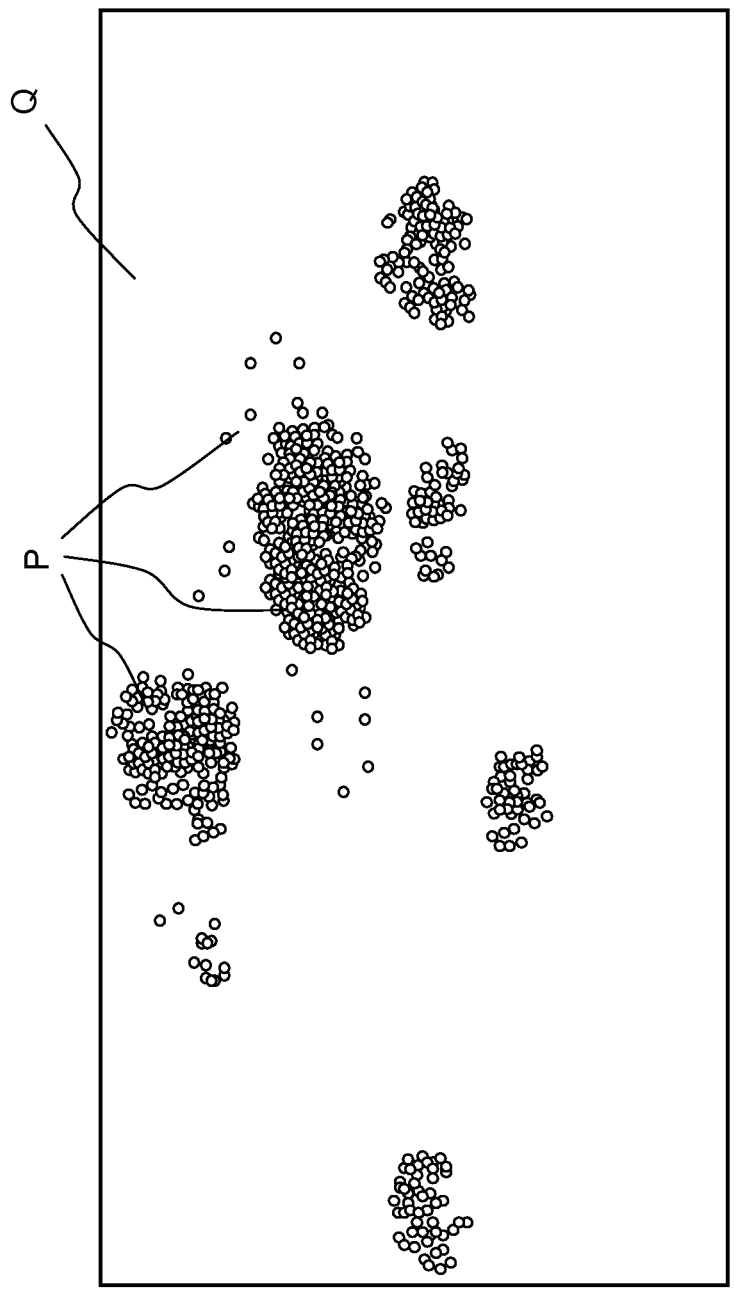
FIG. 5 is an explanatory diagram showing an example of a gaze distribution detected by a gaze direction detection device according to an exemplary embodiment of the present technology.

FIG. 5 is an explanatory diagram showing an example of the gaze distribution detected by the gaze direction detection device according to the exemplary embodiment of the present technology. In FIG. 5, one gaze point P is displayed on virtual plane Q as one circle. Additionally, the gaze distribution may be assumed to be at a position on virtual plane Q or on a plane that is inclined by one degree from a position on virtual plane Q in each of horizontal and vertical directions, for example.

Calculator 150 calculates a correction parameter based on the gaze distribution generated by generator 140 and data of a reference distribution, recorded in memory 170, where a specified direction is set in advance, and outputs the correction parameter to corrector 160. Operation of calculator 150 will be described later.

Corrector 160 corrects the first gaze information output from detector 120 by using the correction parameter output from calculator 150, and outputs the information as the gaze direction of the driver. Corrector 160 is for calculating the correction parameter from the reference distribution that is set in advance and the gaze distribution that is generated by generator 140, and for correcting the first gaze information with the correction parameter. Operation of corrector 160 will be described later.

In the following, operation of calculator 150 will be described in detail.

First, specified direction data will be described. The specified direction data is expressed, for each mounting vehicle, by a value indicating the direction, other than front, in which the driver possibly looks often and the size of the area.

Figure 6:
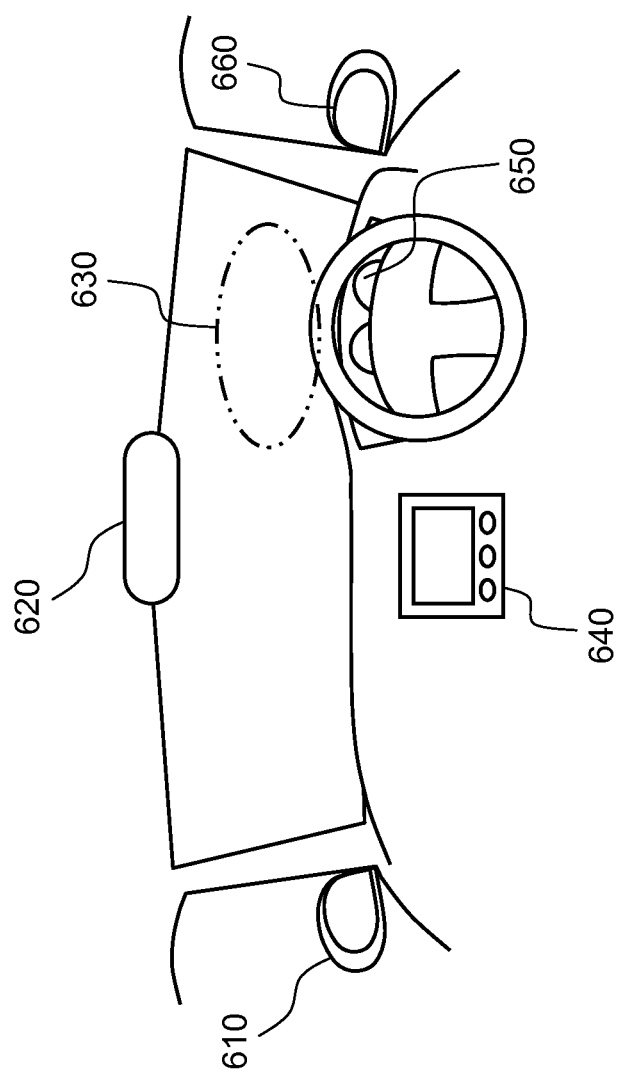
FIG. 6 is an explanatory diagram showing an example of a gaze distribution detected by a gaze direction detection device according to an exemplary embodiment of the present technology.

FIG. 6 is an explanatory diagram showing an example of the gaze distribution detected by the gaze direction detection device. FIG. 6 schematically shows the front inside of the vehicle seen by the driver. As shown in FIG. 6, as for the directions, other than front 630, in which the driver possibly looks often, there may be left side mirror 610, right side mirror 660, rearview mirror 620, various meters 650, car navigation 640, an audio screen (not shown), and the like. Calculator 150 generates, on the virtual plane or the virtual spherical surface three meters in front of the seat, based on the specified direction data, a reference distribution in which areas where the gaze may possibly concentrate on are set.

Figure 7:
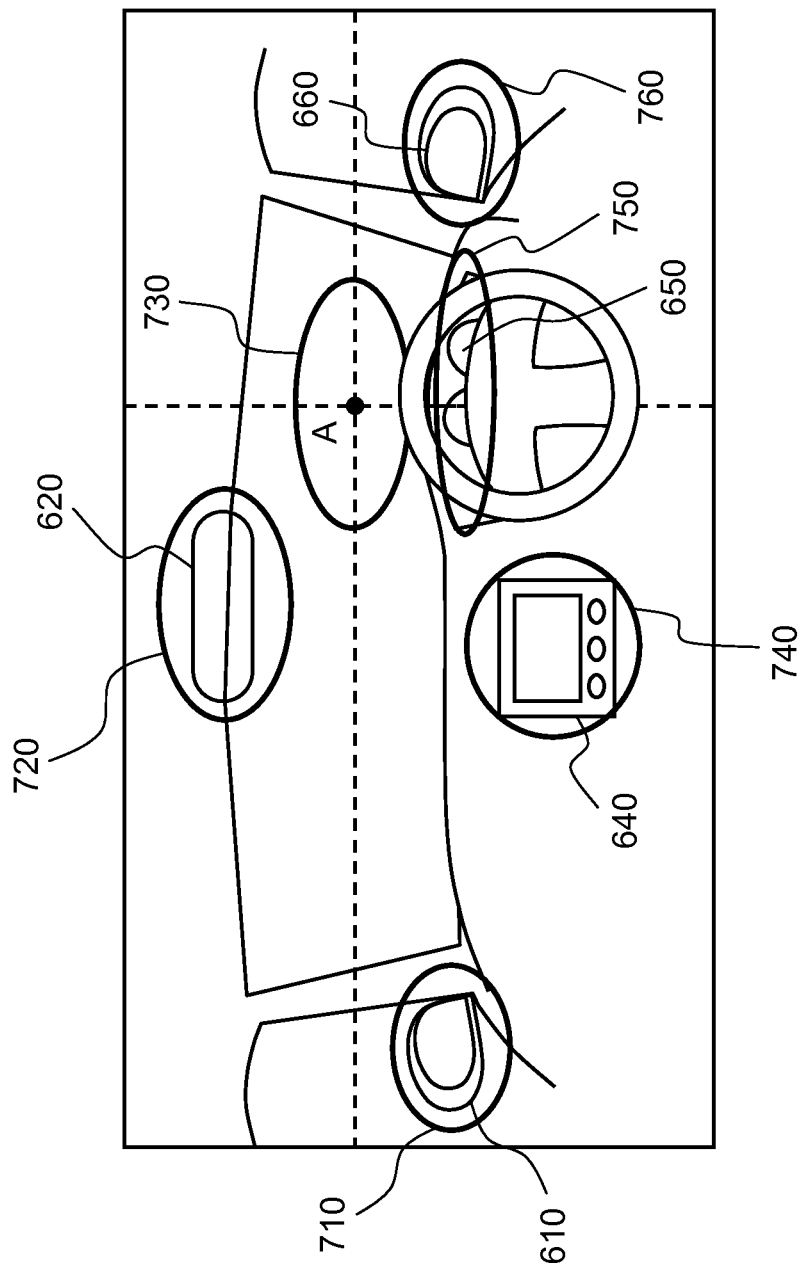
FIG. 7 is an explanatory diagram showing an example of a reference distribution of a gaze direction detection device according to an exemplary embodiment of the present technology.

FIG. 7 is an explanatory diagram showing an example of the reference distribution according to the gaze direction detection device. As shown in FIG. 7, the reference distribution is structured from area 710 surrounding left side mirror 610, area 760 surrounding right side mirror 660, area 720 surrounding rearview mirror 620, area 730 corresponding to front 630, area 740 surrounding car navigation 640, and area 750 surrounding meters 650. Also, in FIG. 7, point A indicates a center of front area 740. Additionally, the reference distribution may be generated in advance and be stored in memory 170.

Calculator 150 obtains, in the gaze distribution generated by generator 140, a center of distribution at a part assumed to be the front.

Figure 8:
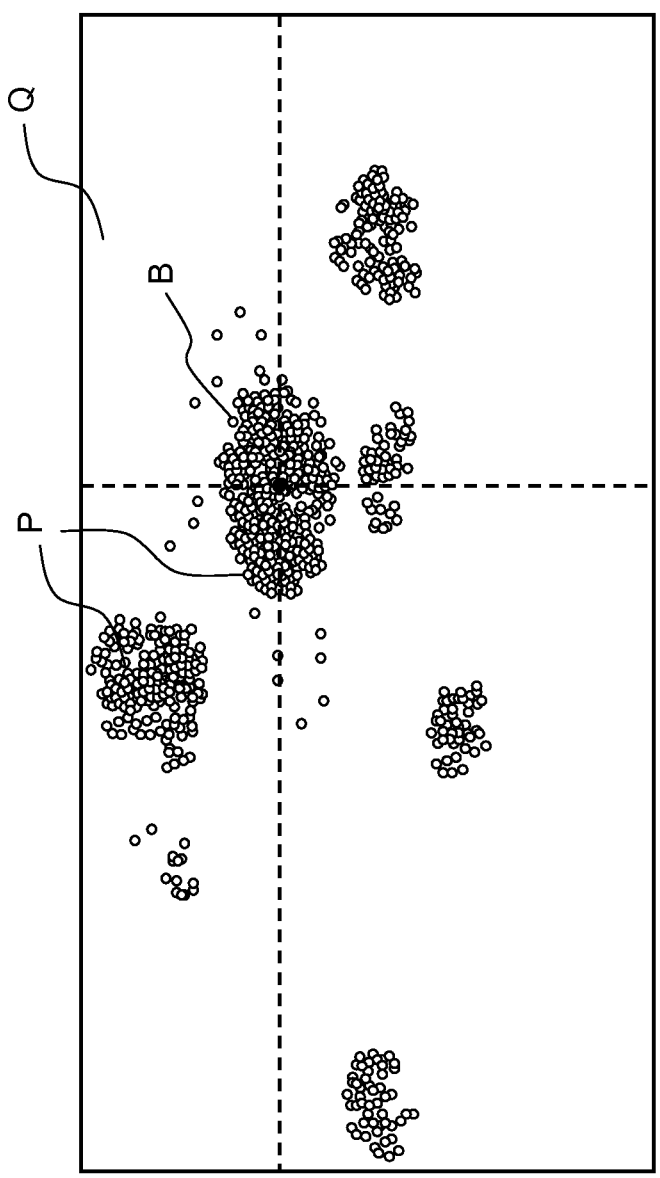
FIG. 8 is an explanatory diagram showing an example of a center point of a gaze distribution of a gaze direction detection device according to an exemplary embodiment of the present technology.

In the case of the gaze distribution in FIG. 5, the center is point B, as shown in FIG. 8. FIG. 8 is an explanatory diagram showing an example of the center point of the gaze distribution according to the gaze direction detection device. In FIG. 8, point B may be obtained by a method for calculating the mean of those, among pieces of gaze information output from the determiner, that are included in the range of 20 degrees in the vertical and horizontal directions, for example.

Calculator 150 performs at least one type of transformation among parallel translation, enlargement/reduction, rotation and the like on the gaze distribution so that the gaze distribution overlaps the reference distribution.

Figure 9:
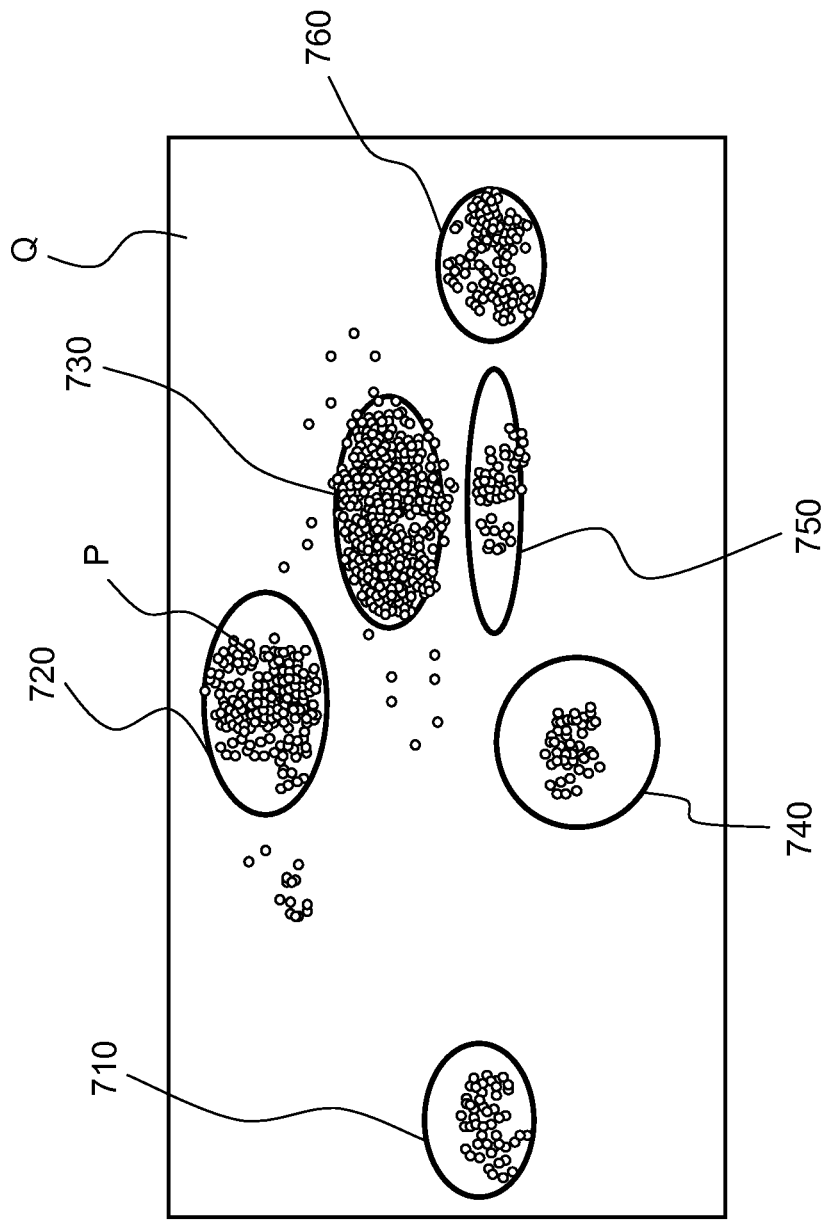
FIG. 9 is an explanatory diagram showing a state where a gaze distribution and a reference distribution are overlapped with each other according to a gaze direction detection device according to an exemplary embodiment of the present technology.

FIG. 9 is an explanatory diagram showing a state where the gaze distribution shown in FIG. 5 and the reference distribution shown in FIG. 7 are overlapped with each other according to the gaze direction detection device. As shown in FIG. 9, calculator 150 calculates, as a correction parameter, the amount of parallel translation (horizontal, vertical), the enlargement/reduction factor, the angle of rotation and the like of the gaze distribution of a case where the gaze distribution and the reference distribution approximately match each other. In the case in FIG. 9, the gaze distribution and the reference distribution may be made to approximately overlap each other by moving the gaze distribution in downward and right directions. The correction parameter may be obtained by calculating the difference of the gaze distribution from the reference distribution. Also, the correction parameter is calculated, at the time of comparison of the gaze distribution and the reference distribution, from at least one parameter selected from the amount of parallel translation in the horizontal direction, the amount of parallel translation in the vertical direction, the enlargement factor, the reduction factor, and the angle of rotation of the gaze distribution with respect to the reference distribution.

Next, an example using a correlation value will be described as an example of a method for determining the overlap between the gaze distribution shown in FIG. 5 and the reference distribution shown in FIG. 7. For example, it is assumed that a value of one is given to one gaze point, and that the value is one when the gaze point is within (overlaps) areas of the reference distribution, and is zero when there is no overlap, and the total number is counted, and the transformation method with the greatest total value is taken as the correction parameter.

Here, in the case of performing enlargement/reduction or rotation, the center of distribution at a part considered to be the front that is obtained in advance is used as the center of enlargement/reduction or the center of rotation. In the present exemplary embodiment, center point B in the front area of the gaze distribution generated by the generator 140 corresponds to the center. After center point B is made to overlap center point A in front area 730 of the reference distribution shown in FIG. 7, transformation processes such as enlargement/reduction and rotation are performed on the gaze distribution, and a transformation process by which the gaze distribution approximately overlaps the reference distribution is identified. Additionally, enlargement/reduction may be performed with the factor being different for four directions of up, down, left and right, or for two directions of horizontal and vertical directions. Also, a plurality of enlargement/reduction factors or rotation angles may be set for each direction.

In this manner, by using the entire distribution, a correction parameter may be obtained for the specified direction even when the gaze is not much directed to some gaze points, such as when driving is performed without using the navigation, for example.

Figure 10:
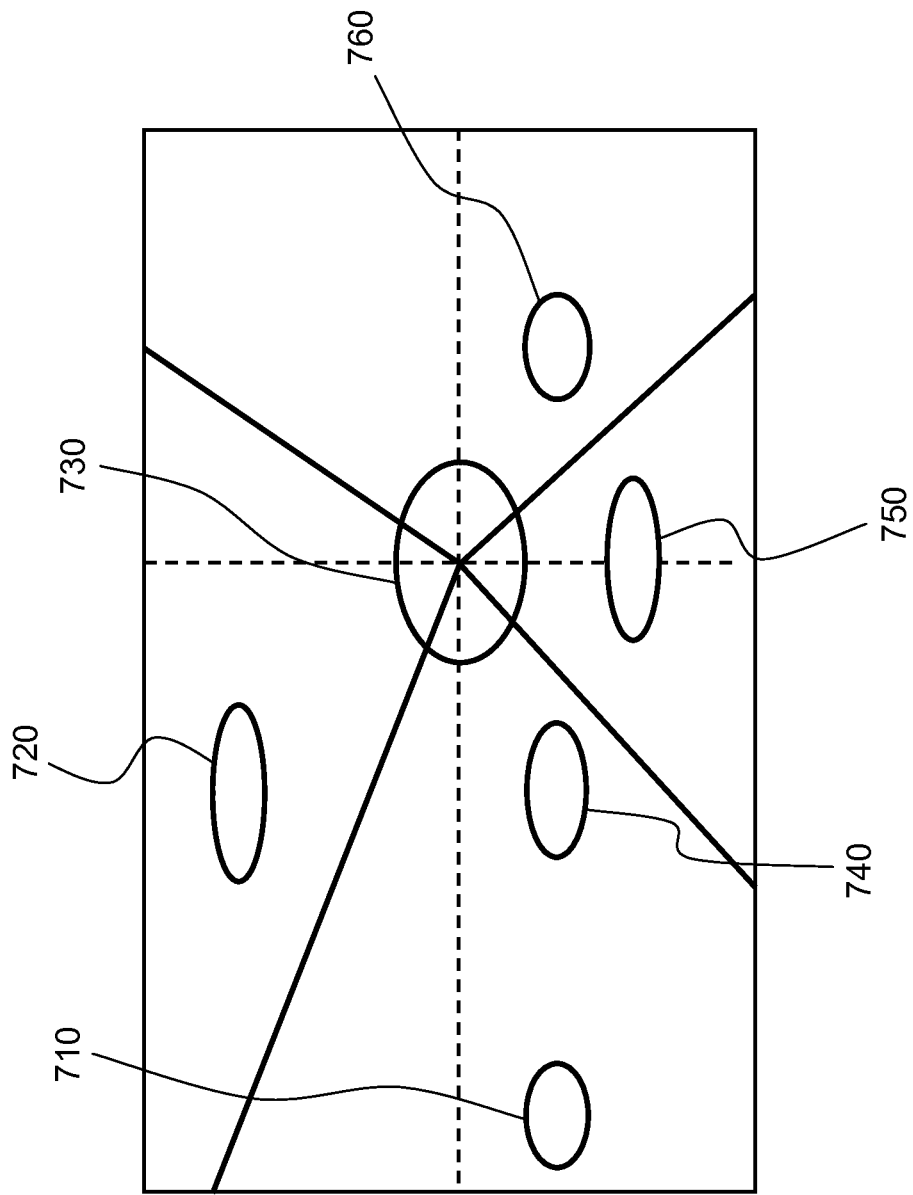
FIG. 10 is an explanatory diagram for describing operation of a corrector of a gaze direction detection device according to an exemplary embodiment of the present technology.

FIG. 10 is an explanatory diagram for describing operation of the corrector. In the exemplary embodiment described above, the enlargement/reduction factor is obtained based on vertical and horizontal division with the front defined as the center, but this is not restrictive. For example, as shown in FIG. 10, the enlargement/reduction factor or the angle of rotation may be obtained by dividing the areas along the directions from the center.

In the following, operation of corrector 160 will be described in detail with reference to FIG. 11.

Figure 11:
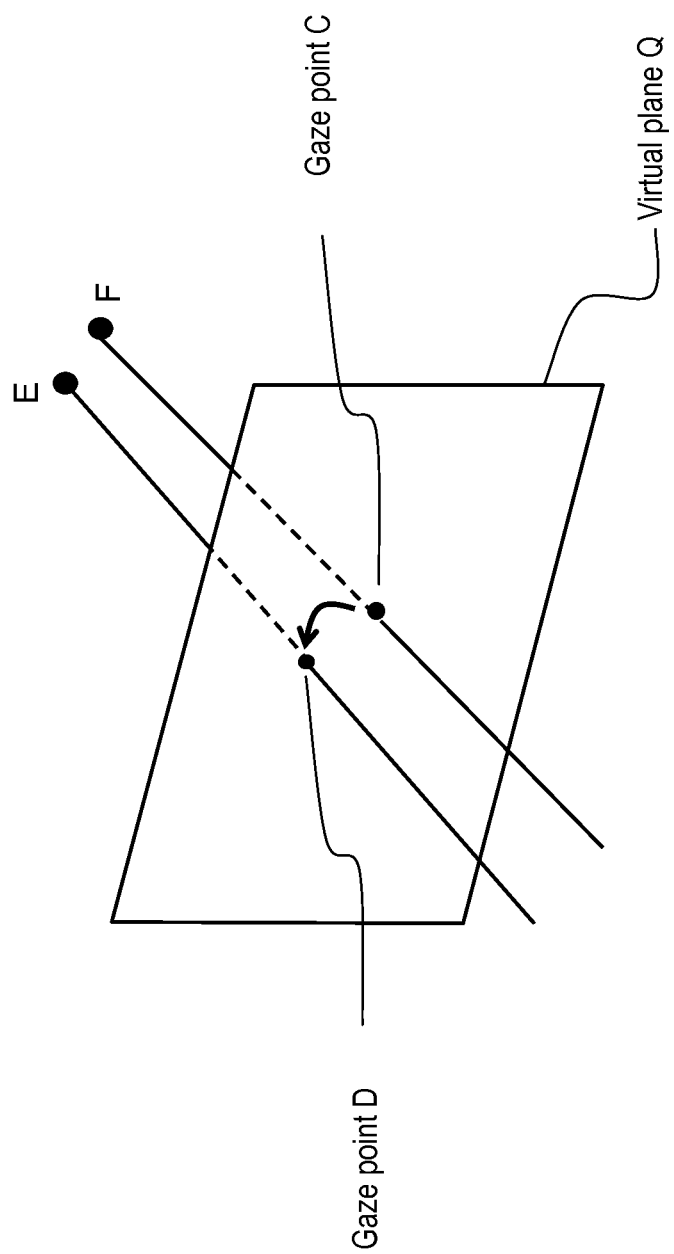
FIG. 11 is an explanatory diagram showing an example of division of an area at the time of detection according to a gaze direction detection device according to an exemplary embodiment of the present technology.

FIG. 11 is an explanatory diagram showing an example of division of an area at the time of detection according to the gaze direction detection device of the present technology, and is a diagram for describing the operation of corrector 160.

First, as with generator 140, corrector 160 obtains gaze point C as an intersection point with virtual plane Q, based on the gaze direction and the viewpoint position which are input from detector 120.

Next, corrector 160 performs correction by moving gaze point C to gaze point D based on the amount of translation, the enlargement/reduction factor, the angle of rotation and the like that is input as the correction parameter by calculator 150. Furthermore, a straight line that passes through reference viewpoint position E set in advance and gaze point D is obtained, and the orientation (angle) of the straight line from the reference viewpoint position is output as the gaze direction after correction. At this time, the direction of the center of the distribution near the front described above may be used as a reference, and a different correction parameter may be used according to whether the direction of the straight line is upward, downward, leftward or rightward from the reference direction. The direction the driver is actually looking may be obtained by such a corrected gaze direction.

As described above, in the present exemplary embodiment, detector 120 detects the gaze information of a driver, determiner 130 determines whether the gaze information indicates that the driver is gazing, generator 140 generates the gaze distribution from the gaze information output by the determiner, calculator 150 calculates the correction parameter based on the difference between the gaze distribution generated by the generator and the reference distribution, and corrector 160 corrects the gaze information detected by the detector by the correction parameter.

Accordingly, detection of a gaze direction which is not easily affected by individual differences may be performed without performing calibration in advance. Detection of the gaze direction which is not easily affected by individual differences may also be performed in a case where an audio or navigation appliance is not operated.

Other Exemplary Embodiments

The first exemplary embodiment has been described above as an example of application of the present technology. However, the present technology is not limited to the above, and may be applied to exemplary embodiments which have been subjected to modifications, substitutions, additions, omissions, and the like as required. Also, a new exemplary embodiment may be achieved by combining the structural elements described in the first exemplary embodiment described above.

Additionally, the correction parameter immediately before stopping may be recorded in a non-volatile memory, and be used the next time driving is performed by the driver. In this case, whether the driver is the same as the driver immediately before stopping may be determined based on whether the seat, the steering wheel, or the mirrors are adjusted, for example. Also, determination may be performed by performing authentication based on the iris or the face image by using an image captured by imaging unit 110. This allows highly accurate detection of the gaze direction from immediately after the start of the vehicle in the case where the driver is the same.

Also, in the case where there is a plurality of drivers, the correction parameters of respective drivers may be recorded in the memory, and the correction parameter of a person who sat in the driving seat may be selected and be used. For example, determination of the driver may be performed by authentication based on the iris or the face image by using the image captured by imaging unit 110 as described above.

As described above, the exemplary embodiment considered by the applicant to be a best mode and other exemplary embodiments are provided with reference to the appended drawings and detailed description. These are provided for the purpose of exemplifying the subject matters of claims for persons skilled in the art by reference to the particular embodiment. Therefore, the structural elements shown in the appended drawings and described in the detailed description may include not only structural elements that are essential for solving the problem but also other structural elements. Hence, that these non-essential structural elements are shown in the appended drawings and described in the detailed description does not cause these structural elements to be immediately recognized as being essential. Furthermore, various modifications, substitutions, additions, and omissions may be performed regarding the aforementioned exemplary embodiment within a range of claims and equivalents to the claims.

The present technology may be applied to a device for detecting a gaze direction of a driver. Application is also possible to detection of a gaze direction in a driving support device or a driving state monitoring device for estimating the driving state of a driver (whether he/she is being careless or not), for detecting insufficient safety confirmation, or for issuing a warning regarding a dangerous object which is probably not noticed judging from the direction of the gaze, for example.

What is claimed is:

1. A gaze direction detection device comprising:
   a detector for detecting a gaze of a driver over a predetermined period of time;
   a determiner for outputting second gaze information indicating that the driver is gazing, from first gaze information detected by the detector;
   a generator for generating a gaze distribution from the second gaze information output by the determiner; and
   a corrector for correcting the first gaze information detected by the detector,
   wherein the corrector calculates a center of a reference distribution that is set in advance and a center of the gaze distribution generated by the generator, and causes the center of the reference distribution and the center of the gaze distribution to overlap each other, and then calculates a correction parameter based on a difference between the reference distribution and the gaze distribution, and corrects the first gaze information with the correction parameter.

2. The gaze direction detection device according to claim 1, wherein the correction parameter is calculated, at a time of comparison of the gaze distribution and the reference distribution, from at least one parameter selected from an amount of parallel translation in a horizontal direction, an amount of parallel translation in a vertical direction, an enlargement factor, a reduction factor, and an angle of rotation of the gaze distribution with respect to the reference distribution.

3. A gaze direction detection method to be performed by a generator for outputting, from first gaze information of a driver over a predetermined period of time detected by a detector, second gaze information indicating that the driver is gazing, and then generating a gaze distribution from the second gaze information, and the method being performed by a corrector for correcting the first gaze information detected by the detector,
   wherein, when correcting the first gaze information detected by the detector, the corrector causes a center of a reference distribution that is set in advance and a center of the gaze distribution generated by the generator to overlap each other, and then calculates a correction parameter based on a difference between the reference distribution and the gaze distribution, and corrects the first gaze information with the correction parameter.

4. The gaze direction detection method according to claim 3, wherein the correction parameter is obtained by calculating the difference of the gaze distribution from the reference distribution.

5. The gaze direction detection method according to claim 3, wherein the correction parameter is calculated, at a time of comparison of the gaze distribution and the reference distribution, from at least one parameter selected from an amount of parallel translation in a horizontal direction, an amount of parallel translation in a vertical direction, an enlargement factor, a reduction factor, and an angle of rotation of the gaze distribution with respect to the reference distribution.

* * * * *